United States Patent [19]

Hannaford et al.

[11] Patent Number: 5,054,921
[45] Date of Patent: Oct. 8, 1991

[54] DOPPLER-FREE SPECTROSCOPY

[75] Inventors: Peter Hannaford, Mount Waverley; David S. Gough, Blackburn, both of Australia

[73] Assignee: Commonwealth Scientific and Industrial Research Organisation, Australia

[21] Appl. No.: 374,015

[22] Filed: Jun. 30, 1989

[51] Int. Cl.⁵ .......................... G01J 3/42; G01N 21/62
[52] U.S. Cl. ..................... 356/311; 356/314; 356/300
[58] Field of Search .............. 356/300, 311, 313, 314, 356/319, 346, 349

[56] References Cited

U.S. PATENT DOCUMENTS 4,817,101 3/1989 Wyeth et al. .................. 356/345

Primary Examiner—F. L. Evans
Attorney, Agent, or Firm—Sughrue, Mion, Zinn, Macpeak & Seas

[57] ABSTRACT

A substantially Doppler-free spectrum of an element in a sputtered vapor is obtained by generating the sputtered vapor of the sample in a sputtering cell containing a rare gas and obtaining a saturated absorption spectrum for the vapor. The vapor is sputtered from a cathode including the sample and the pressure of the rare gas in the sputtering cell and the chopping frequency of a laser pump beam employed to obtain the saturated absorption spectrum are selected to reduce the number of detected velocity changing collisions in the cell to substantially eliminate any background Doppler-broadened component from the saturated absorption spectrum which is thereby a substantially Doppler-free spectrum.

18 Claims, 2 Drawing Sheets

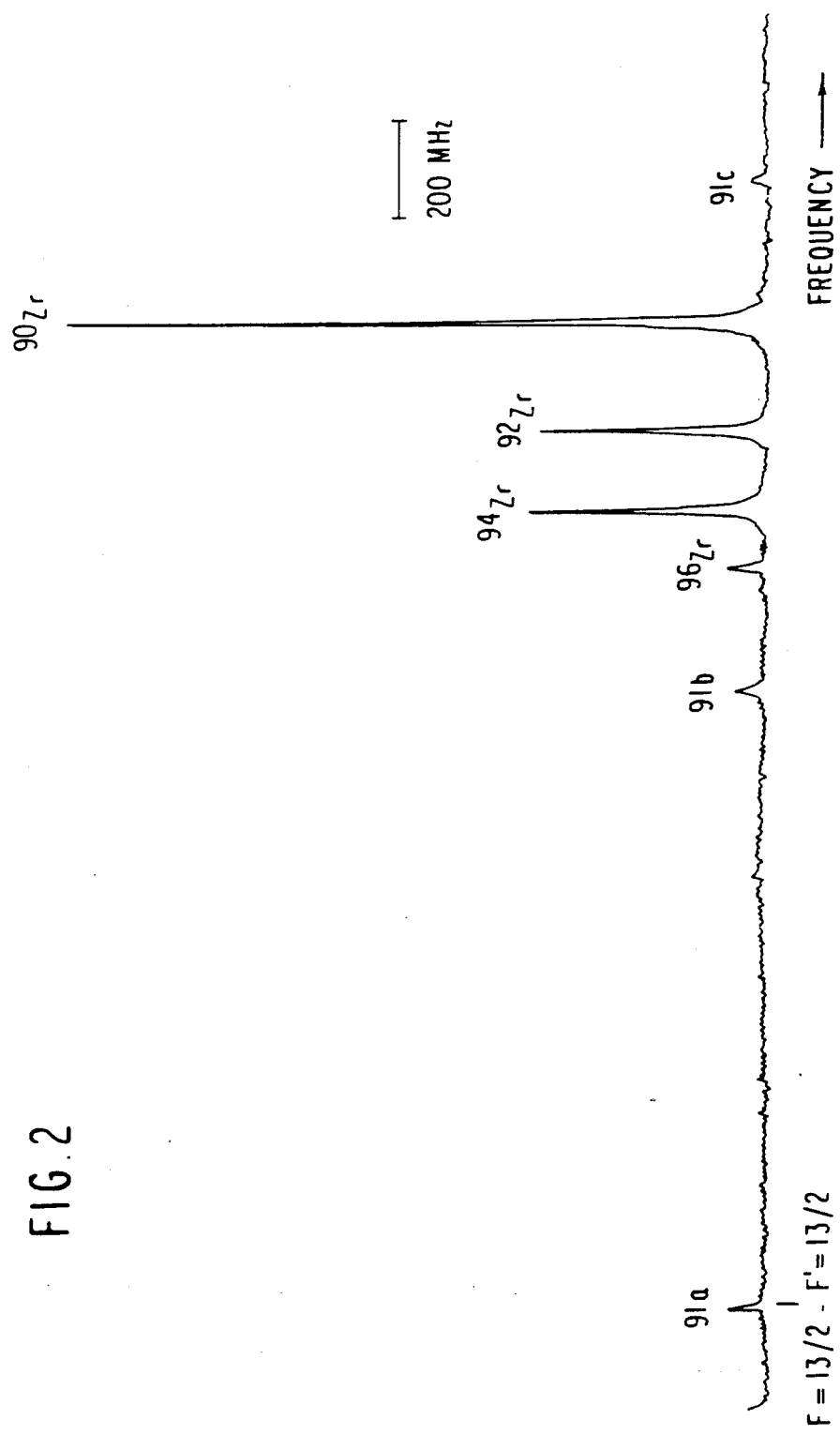

DOPPLER-FREE SPECTROSCOPY

FIELD OF THE INVENTION

This invention relates generally to Doppler-free spectroscopy and more particularly to the derivation of a substantially Doppler-free saturated absorption spectrum in sputtered atomic vapours, especially for use in isotope analysis.

BACKGROUND ART

Isotope analyses based on optical spectroscopic techniques such as atomic absorption or atomic emission have to date been confined to elements such as Li, B, U, Pb and Hg for which the isotope shifts are larger than or comparable with the Doppler width of the transition (of the order of 1 GHz at 300K). Most elements, however, have isotope shifts of the order of only a few hundred megahertz, which precludes the use of Doppler-limited spectroscopic techniques.

The availability of narrow-band tunable laser sources in recent years has led to the development of a number of very elegant techniques for eliminating Doppler broadening in an atomic vapour, thereby allowing the detailed structure of spectral lines to be investigated. One such technique is Doppler-free saturated absorption spectroscopy, described in Hänsch et al, Phys. Rev. Lett. 27, 707 (1971). With this technique two counter-propagating beams from a narrow-band tunable dye laser are directed into opposite ends of a vapour cell and the saturating effect of the first beam (the pump) on the transmission of the second beam (the probe) by the vapour is detected as the frequency of the laser is scanned through a selected atomic transition. Since the detected signal originates only from atoms which can interact with both laser beams, i.e. atoms which have zero velocity component along the direction of propagation of the laser beams, a Doppler-free spectrum results.

In conventional saturated absorption experiments, the element to be investigated is usually either in the form of a gas or it is converted to an atomic vapour by thermal evaporation in an evacuated cell. Thus, until recently, saturated absorption spectroscopy had been restricted largely to the rare gases and the more volatile elements, such as the alkali metals and alkaline earths, that can be readily vaporised at moderate temperatures. An alternative approach, first described by Gerstenberger et al, Optics Commun. 31, 28 (1979), is to generate the atomic vapour by cathodic sputtering in a hollow-cathode discharge. With this method the element to be investigated is made the cathode of a hollow-cathode discharge and atoms are ejected from the cathode surface by ion bombardment to form an atomic vapour. The sputtering method of vaporisation has the advantage that it is readily applicable to essentially any element, including highly refractory elements (such as Zr) that are very difficult or impossible to vaporise by conventional thermal means. However, with the sputtering method the atomic vapour is necessarily generated in the presence of a rare gas, and the quality of the Doppler-free spectra is degraded by effects of velocity-changing collisions (VCC). These collisions tend to redistribute the velocities of the atoms over the original Maxwellian distribution and thereby introduce broad background pedestals as well as additional broadening to the narrow Doppler-free components. Such effects can be particularly severe for transitions from a ground (or near-ground) level, because of the long time available for the atoms to undergo VCC.

Several techniques have been devised for reducing the effects of VCC in Doppler-free spectroscopy in hollow-cathode discharges. According to one proposal, polarization intermodulated excitation spectroscopy (Dabkiewicz and Hänsch, Optics Commun. 38, 351 (1981)) or polarization spectroscopy is used to probe the orientation of atoms in the vapour, so that those atoms which have undergone VCC no longer contribute to the observed signal if their orientation has been destroyed by the VCC. A second technique (Gough and Hannaford, Optics Commun. 55, 91 (1985)), which has been used in saturated absorption and intermodulated fluorescence spectroscopy, is to operate the hollow-cathode discharge at sufficiently high current density to shorten the lifetime of the lower level, thereby reducing the time available for VCC to take place A further technique (Kröll and Persson, Optics Commun. 54, 277 (1985)) which has been suggested for use in saturated absorption spectroscopy is to choose a suitably high chopping frequency for the laser pump beam such that the phase of the broad pedestal component lags that of the narrow Doppler-free component, thereby allowing the narrow component to be isolated (or partially isolated) by the phase-sensitive detector.

SUMMARY OF THE INVENTION

It is an object of the invention to obtain a substantially Doppler-free spectrum of an element in a sputtered vapour, which spectrum is adaptable to accurate measurements of the intensitites of isotype components for isotope analysis.

The invention therefore provides a method of obtaining a substantially Doppler-free spectrum of a sample, which includes generating a sputtered vapour of the sample in an evacuable sputtering cell containing rare gas such as argon or xenon and obtaining a saturated absorption spectrum for the vapour. The vapour is sputtered from a cathode including the sample. The pressure of rare gas in the sputtering cell and the chopping frequency of a laser pump beam employed to obtain the saturated absorption spectrum are selected to reduce the number of detected velocity changing collisions in the cell to substantially eliminate any background Doppler-broadened component from the saturated absorption spectrum, which is thereby a substantially Doppler-free spectrum.

The vapour is advantageously sputtered from an open electrode, for example a planar electrode.

The pressure of rare gas in the cell is preferably less than 10 Torr, more preferably less than 1 Torr. Most preferably, this pressure is of the order of 0.1 Torr.

The chopping frequency is advantageously greater than 50 kHz, most preferably of the order of 100 kHz.

Also provided by the invention is a method of determining isotopic abundances for a sample, which includes generating a sputtered vapour of the sample in an evacuable sputtering cell containing rare gas and obtaining a saturated absorption spectrum for the vapour. The vapour is sputtered from a cathode, preferably an open cathode, including the sample. The pressure of rare gas in the sputtering cell and the chopping frequency of a laser pump beam employed to obtain the spectrum are selected to reduce the number of detected velocity changing collisions in the cell to substantially eliminate any background Doppler-broadened component from the saturated absorption spectrum, which is thereby a substantially Doppler-free spectrum for the sample having discrete lines identifiable with respective isotopes of the sample. This method further comprises calculating the isotopic abundances from the intensities of the isotope components, with corrections as necessary for effects dependent on density of absorbing atoms in the cell, laser intensity, isotope mass, and, with isotopes having a nuclear spin, hyperfine structure.

The invention still further affords apparatus for obtaining a substantially Doppler-free spectrum of a sample, comprising:

a sputtering cell having an open sputtering cathode of the sample for generating in the cell a sputtered vapour of the sample;

a spectroscopic arrangement to obtain a saturated absorption spectrum of the vapour in the cell, said arrangement including means to chop an incident light beam for said cell, wherein in use the pressure in said sputtering cell and the chopping frequency of an incident beam employed to obtain said spectrum are controlled to reduce the number of detected velocity changing collisions in said cell to substantially eliminate any background Doppler-broadened component from said saturated absorption spectrum, which is thereby a substantially Doppler-free spectrum.

BRIEF DESCRIPTION OF THE DRAWINGS

The invention will now be further described, by way of example only, with reference to the accompanying drawings, in which:

FIG. 2 depicts the saturated absorption spectrum for the Zr I 612.7 nm transition obtained by the method of the invention.

BEST MODES OF CARRYING OUT THE INVENTION

Figure 1:
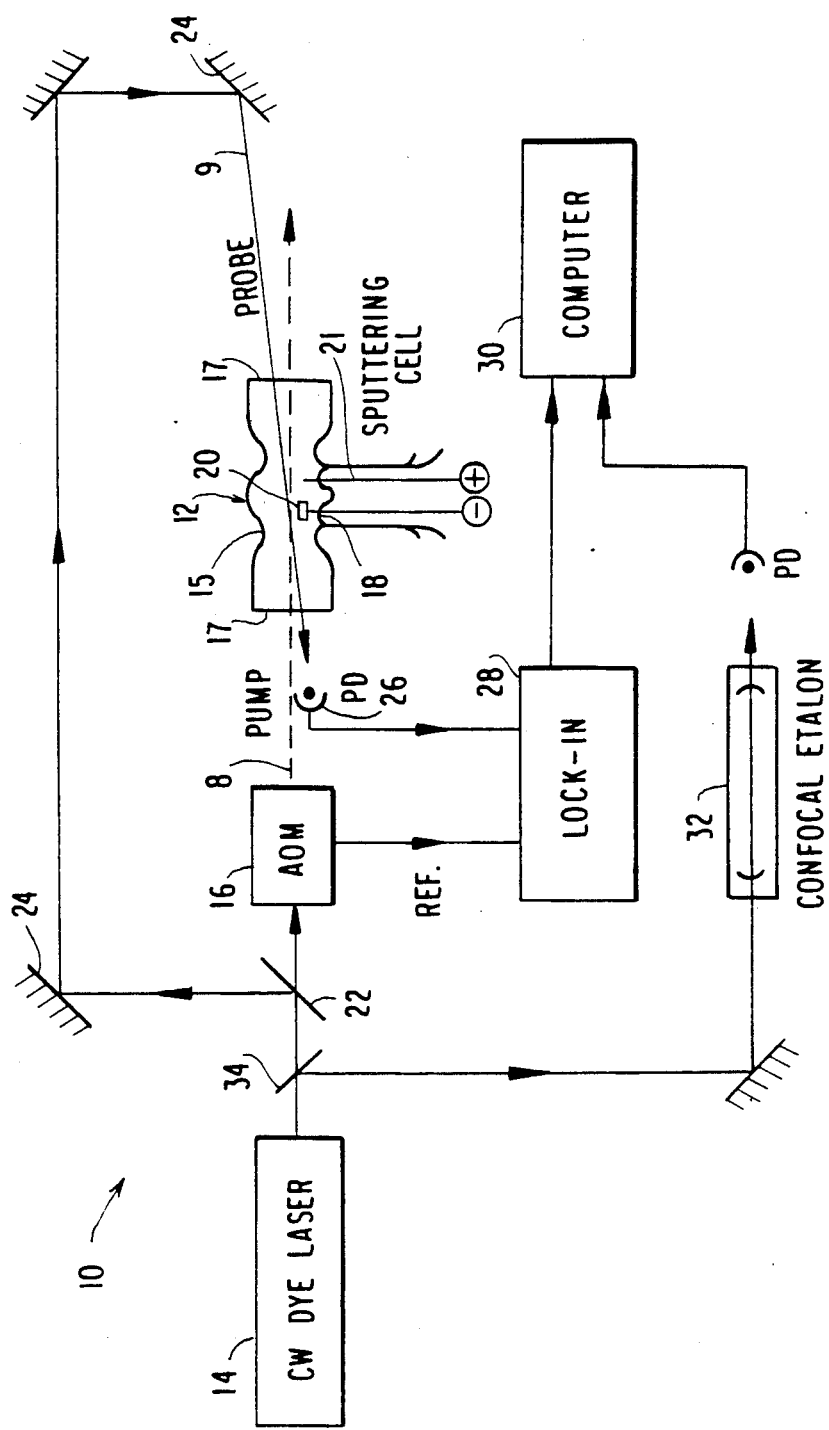
FIG. 1 is an optical ray diagram of apparatus according to the invention.

The illustrated apparatus 10 includes an evacuable sputtering cell 12 of generally tubular configuration, a laser 14 oriented to direct an incident light beam 8, known as the pump beam, along the axis of cell 12, and an acousto-optic modulator 16 to chop the pump beam. Cell 12 has a central lateral port 18 to sealingly but demountably receive an open sputtering cathode 20 which includes the sample of interest. Cathode 20 is more particularly a planar cathode which permits the discharge to be operated at very low pressure of rare gas. Laser 14, which is conveniently a narrow-band CW tunable dye laser, is tuned close to a resonance with a transition corresponding to the element under investigation.

A partial beamsplitter 22 and a succession of mirrors 24 direct a second laser beam 9, known as the probe beam, in the opposite direction through cell 12. This probe beam 9 is detected by a fast photodiode 26 with an associated lock-in amplifier 28 which is referenced to the chopping frequency of modulator 16. The amplifier output is processed by computer 30. A confocal etalon 32 receives a further portion of the laser output via a second partial beamsplitter 34 to provide markers for frequency calibration of the scans.

Cell 12 includes an anode which is conveniently in the form of a wire 21 and ports for admitting a suitable rare gas such as xenon or argon through the cell and controlling the rare-gas pressure below atmospheric pressure. Necks 15 confine sputtered vapour and prevent contamination of windows 17.

The general arrangement depicted in FIG. 1 is suitable for performing Doppler-free saturated absorption spectroscopy on the vapour sputtered from cathode 20, but differs structurally from conventional equipment used for such spectroscopy by having an open cathode rather than the traditional hollow cathode. By "open" is meant that the cathode itself does not wholly or partially enclose a space or passage containing sputtered species. According to the principles of saturated absorption spectroscopy, when the laser is tuned exactly to resonance, the saturating effect of the (modulated) pump beam increases the transmission of the probe beam, which is detected as a small modulation on the probe beam by the lock-in amplifier. The only atoms which interact with both laser beams and hence contribute to the modulated component of the probe signal detected by the lock-in are those with zero velocity component along the direction of propagation of the laser beams and hence the signal should in principle be free from Doppler broadening.

As mentioned, it has been found that, although individual isotopic peaks can be resolved using conventional saturated absorption spectroscopy in a hollow-cathode discharge, a significant Doppler-broadened pedestal remains and there is therefore insufficient fine resolution for the accurate measurement of intensities of components in the spectrum to be used for isotopic analysis. This pedestal arises from velocity-changing collisions due to the rare gas in the sputtering cell. It has been appreciated that this problem is overcome by employing a planar sputtering cathode which allows substantially lower pressures to be used, and by then setting the cell pressure and the chopping frequency of modulator 16 so as to reduce the number of detected velocity changing collisions in cell 12 to substantially eliminate any background Doppler-broadened component from the saturated absorption spectrum.

It is found that a rare gas pressure in cell 12 of the order of 0.1 Torr and a chopping frequency of the order of 100 kHz sufficiently reduce the number of detected collisions to substantially eliminate the background Doppler-broadened components and obtain a spectrum of very high resolution. In addition, the low pressures at which the planar-cathode discharge can be operated reduce the effect of phase-changing collisions (pressure broadening) and permit very narrow Doppler-free resonances to be recorded (typically of the order of 5 MHz for transitions involving long-lived atomic levels and allowing 2 MHz for the bandwidth of the laser), and the high chopping frequency allows excellent signal-to-noise.

By way of example, FIG. 2 depicts the spectrum for the Zr I 612.7 nm ($a^3F_4 - z^3F^o_4$) transition obtained with the apparatus illustrated in FIG. 1, utilising a xenon pressure of 0.10 Torr, a discharge current of 2 mA and a chopping frequency of 100 kHz. The laser intensities were 0.3 mW mm$^{-2}$ for the pump beam and 0.04 mW mm$^{-2}$ for the probe beam. Single 100 s scans were employed. The width of the narrow Doppler-free components in FIG. 2 is only 7 MHz FWHM, which allows all of the four even isotope components as well as a number of the hyperfine components from the 11% abundant odd isotope $^{91}$Zr to be clearly resolved. This width is to be compared with the Doppler width of the transition, about 700 MHz. Upon lowering the laser intensity to reduce saturation broadening, the width of the Doppler-free components reduces to about 3.5 MHz, which can be accounted for totally in terms of contributions from natural broadening associated with the lifetime of the upper level (0.4 MHz), pressure broadening in the xenon gas (~1 MHz) and the laser bandwidth (~2 MHz). In particular, any extraneous broadening associated with the discharge itself is negligibly small.

A Doppler-free spectrum such as that in FIG. 2 contains considerable spectroscopic information. First, the positions of the different isotope components allow precise determination of the isotope shifts of the transition. Secondly, the positions of the hyperfine components of the odd isotope $^{91}$Zr permit a precise determination of the hyperfine interaction constants for the upper and lower levels. Thirdly, the width and position of the individual components studied as a function of rare-gas pressure provide information on the pressure broadening and shift of the transition by the rare gas. Finally, the relative intensities of the various isotope components allow a quantitative determination of the abundances of the isotopes in natural zirconium (51.5% $^{90}$Zr, 11.3% $^{91}$Zr, 17.2% $^{92}$Zr, 17.3% $^{94}$Zr and 2.8% $^{96}$Zr), when proper allowance is made for the effects of the density of absorbing atoms in the cell, laser intensity, differences in the masses of the isotopes, and for effects of hyperfine structure in the $^{91}$Zr isotope. Thus saturated absorption spectroscopy in a sputtered vapour provides the basis of a novel high resolution optical technique for isotopic analysis in a wide range of elements, including highly refractory elements such as Zr.

Turning specifically to the determination of isotopic abundance, for the example spectrum of FIG. 2, it can be demonstrated that the ratios of isotope components can be derived from the following formula for the peak intensity of a saturated absorption signal for an isotope i:

$$S_i = \exp\left\{-\left[k_{0i}l\frac{1}{(1 + I_p/I_{sat})^{\frac{1}{2}}} + k^{B_i}l\right]\right\} - \exp\{-[k_{0i}l + k^{B_i}l]\} \quad (1)$$

$k_{0i}$ = peak absorption coefficient for isotope i $\alpha\ N_i f / \Delta\nu_D$ $\alpha\ a_i \mu_i^{\frac{1}{2}} M_i^{\frac{1}{2}} f$ $k^{B_i}$ = background contribution to the absorption coefficient from other isotopes
$I_p$ = intensity of pump beam
$I_{sat}$ = saturation intensity for isotope i
$l$ = path length $N_i$ = number density of absorbing atoms $\alpha\ a_i \dot{D}_i^{-1}$ for isotope i
$a_i$ = isotope abundance
$D_i$ = diffusion coefficient of isotope i in the rare gas $\alpha\ \mu_i^{-\frac{1}{2}}$ $\mu_i$ = reduced mass of isotope i
$\Delta\nu_D$ = Doppler width $\alpha\ M_i^{-\frac{1}{2}}$
$M_i$ = mass of isotope i
$f_i$ = oscillator strength for isotope i Equation (1) is valid for the case of a very weak probe beam, a moderately weak pump beam, and moderately low absorption levels, such that the saturating effect of the pump beam can be assumed to be constant throughout the vapour.

For a pair of even isotopes (nuclear spin I=O; $f_i$ and also $I_{sat}$ same for both isotopes), the ratio of intensities of the isotope components may be expressed as:

$$\frac{S_1}{S_2} = \frac{k_{0i}}{k_{02}}\left\{1 - \left[\frac{1}{2}(k_{01}l + k_{02}l)\left(1 + \frac{1}{(1 + I_p/I_{sat})^{\frac{1}{2}}}\right) + (k^{B1}l - k^{B2}l)\right] + \ldots\right\} \quad (2)$$

For a pair of isotopes consisting of one even isotope and one odd isotope (e.g., $^{91}$Zr, nuclear spin I=5/2, F=I+J), $f_i$ and also $I_{sat}$ are not necessarily the same as for both isotopes and the ratio is given by:

$$\frac{S_1^{91}}{S_2^{even}} = \frac{k_{01}^{91}}{k_{02}^{even}} \cdot \frac{1 - [1 + I_p/I_{sat}^{even}]^{-\frac{1}{2}}}{1 - [1 + I_p/I_{sat}^{91}]^{-\frac{1}{2}}} \{1 - \ldots\} \quad (3)$$

For Zr 612.7 nm ($a^3F_4 - z^3F_4$) and F=13/2−F'=13/2 hyperfine component (component 91a in FIG. 2), $N_{F=13/2}^{91}/N_{ALL}{}^{F^{91}} = 7/27$ (equilibrium)

$f_1^{91}/f_2^{even} = 12/13;\ I_{sat}^{91}/I_{sat}^{even} \approx 1$

The following table compares the isotopic abundance of natural zirconium as determined from a number of spectra similar to that of FIG. 2 with four recognized determinations employing mass spectrometry with calibrating standards. The comparative results are satisfactory.

| | Isotopic Abundance of Natural Zirconium** | | | | |
|---|---|---|---|---|---|
| | $^{90}$Zr | $^{91}$Zr | $^{92}$Zr | $^{94}$Zr | $^{96}$Zr |
| White & Cameron (1949)* | 51.46% | 11.23% | 17.11% | 17.40% | 2.80% |
| Drawin (1958)* | 51.12(11) | 11.22(5) | 17.40(4) | 17.57(4) | 2.79(10) |
| Murthy (1963)* | 51.5 | 11.22 | 17.10 | 17.38 | 2.80 |
| Shima (1978)* | 51.45(6) | 11.320(15) | 17.189(21) | 17.283(21) | 2.759(4) |
| This work - laser spectroscopy | 51.4(3) | 11.5(5) | 17.1(2) | 17.2(2) | 2.75(5) |

*mass spectrometry (using calibrating standards)
**numbers in parenthesis represent uncertainty in last digit The present accuracy is considered to be 0.5% for $^{90}$Zr/$^{92}$Zr; 1% for $^{94}$Zr/$^{92}$Zr; 2% for $^{96}$Zr/$^{92}$Zr; and 5% for $^{91}$Zr/$^{92}$Zr.

It will be appreciated that the described technique of isotopic analysis greatly expands the range of elements accessible by optical spectroscopy in principle to almost any solid element in the periodic table including refractory elements and elements with small isotope shifts. The technique potentially has an advantage over the conventional technique of mass spectrometry in that it is totally element-selective as well as isotope-selective and hence should not require high purity samples: there should therefore be no requirement for expensive and time-consuming chemical separation of samples prior to analysis. The technique of the invention should be adaptable to a small robust laser isotopic analysis system, based on miniature solid state lasers, suitable for rapid on-line analysis in the field.

the laser-atom interaction, if all relevant parameters are known, or empirically by extrapolating to zero laser pump intensity.

For the strongest $^{91}$Zr hyperfine component of the 612.7 nm $a^3F_4 - z^3F_4$ transition, i.e. $F = 13/2 \rightarrow F' = 13/2$ (labelled 91a in FIG. 2), $I_{sat}$ is found (from linewidth—versus—laser intensity measurements) to be approximately the same as for the even Zr isotopes.

(3) MASS DEPENDENT EFFECTS

The signal intensity $S_i$ depends on the number of atoms

| DETERMINATION OF ISOTOPIC RATIOS FOR Zr | | | | |
|---|---|---|---|---|
| | $^{91}$Zr/$^{92}$Zr | $^{90}$Zr/$^{92}$Zr | $^{94}$Zr/$^{92}$Zr | $^{96}$Zr/$^{92}$Zr |
| Ratios of signal intensities extrapolated to zero absorbance | $0.166 \pm .0025$ | $2.939 \pm .015$ | $1.014 \pm .010$ | $0.165 \pm .003$ |
| Extrapoloated to zero pump laser intensity | $0.1585 \pm .008$ | — | — | — |
| Corrected for mass effects | $0.1599$ | $2.991 \pm .015$ | $0.997 \pm .010$ | $0.160 \pm .003$ |
| Corrected for hyperfine structure effects | $0.1599 \times \frac{27}{7} \times \frac{13}{12} = 0.67 \pm .03$ | — | — | — |

Appendix

In order to convert the original intensity ratios of pairs of isotope components, expressed as equations (2) and (3) above, to isotopic abundance ratios, a number of corrections need to be applied.

(1) ATOM DENSITY DEPENDENT EFFECTS

The ratios of signal intensities of pairs of isotope components $S_1/S_2$ depends on the density of absorbing atoms, according to equations (1)–(3).

Even when the abundances for each of the pairs of isotopes is essentially the same [e.g. for $^{92}$Zr (17.1%) and $^{94}$Zr (17.2%)] so that the peak absorption coefficients for each isotope are about the same ($k_{01} \approx k_{02}$), a significant dependence of $S_1/S_2$ on absorbance can still occur when there are differences in the background absorption contribution from neighbouring isotopes ($k^{B1} \neq k^{B2}$), as is the case for $^{92}$Zr and $^{94}$Zr. This correction can be determined theoretically, if all the relevant parameters are known, or empirically by extrapolating the ratio $S_1/S_2$ to zero atom density or absorbance, where the absorbance can be determined from the transmission of the weak probe beam in the absence of the pump beam. The latter technique was employed in deriving the results given in the Table above.

(2) LASER-INTENSITY DEPENDENT EFFECTS (a) Case of pairs of even isotopes (i.e., no hyperfine structure). For the relatively low laser intensities normally used in laser saturated absorption experiments, the ratio $S_1/S_2$ for even isotopes is independent of the intensity of the pump laser $I_p$ at absorbances near zero [see equation (2)].

(b) Case of pairs of isotopes with one isotope with hyperfine structure. The saturation laser intensity $I_{sat}$ for the odd isotope components is in general not the same as for the even isotope components, and this will affect the ratio of signal intensities for the saturated absorption signals. In addition, optical pumping effects by the pump laser (which alter the population of the lower level of the transition for a given laser pump intensity) will in general not be the same for the odd and even isotope components. These corrections can in principle be made theoretically by detailed modelling of of isotope i having zero velocity component in the direction of the laser beams, which in turn depends on:

(a) the peak absorption coefficient $k_{oi}$, which is inversely proportional to the Doppler width $\Delta v_D$, and hence proportional to $\sqrt{M_i}$ (where $M_i$ is the mass of isotope i).

(b) the steady-state concentration of atoms of isotope i, $N_i$, which is inversely proportional to the diffusion coefficient of the sputtered metal atoms in the environment of the rare gas, and hence proportional to $\sqrt{\mu_i}$, where $\mu_i$ is the reduced mass given by $$\mu_i = \frac{M_i M_g}{M_i + M_g}$$

and $M_g$ is the mass of the rare-gas atoms.

(4) HYPERFINE STRUCTURE EFFECTS

This only affects ratios involving an isotope with nuclear spin (usually an odd isotope). The signal intensity $S_i$ of a given hyperfine component depends on:

(a) the population of the lower hyperfine level relative to the sum of the populations of all the hyperfine levels in the lower J level.

For $F = 13/2$ $F' = 13/2$ hyperfine component of the 612.7 nm ($a^3F_4 - z^3F_4$) transition in $^{91}$Zr (I = 5/2), $$N^{91}_{F=13/2}/N^{91}_{ALL\ F} = \frac{2F+1}{[2I+1][2J+1]} = \frac{7}{27}$$

(b) the peak absorption coefficient $k_o^i$, which is proportional to the oscillator strength of the transition, $f_i$:

For $^{91}$Zr ($F = 13/2 \rightarrow F' = 13/2$) relative to even isotopes of Zr, $$\frac{f_1^{91}(F->F')}{f_2^{even}(J->J')} = (2F+1)(2J'+1)\left\{ \begin{array}{c} FIJ \\ F1J' \end{array} \right\} = \frac{12}{13}$$

for $I = 5/2$, $J = J' = 4$, $F = 13/2$.

In practice, these different correction factors may remain constant for a given set of experimental conditions and may not have to be determined each time. In addition, for highest accuracy, calibrating standards could be used instead of applying corrections, as is common practice in mass spectrometric determination of isotope ratios.

We claim:

1. A method of obtaining a substantially Doppler-free spectrum of a sample, comprising generating a sputtered vapour of the sample in an evacuated sputtering cell and obtaining a saturated absorption spectrum for the vapour, wherein said vapour is sputtered from a cathode including the sample, and the pressure in said sputtering cell and the chopping frequency of an incident laser beam employed to obtain said spectrum are selected to reduce the number of detected velocity-changing collisions in said cell to substantially eliminate any background Doppler-broadened component from said saturated absorption spectrum, which is thereby a substantially Doppler-free spectrum.

2. A method according to claim 1 wherein said vapour is sputtered from an open cathode including the sample.

3. A method according to claim 1 wherein said pressure in said sputtering cell is less than 10 Torr.

4. A method according to claim 1 wherein said pressure in said sputtering cell is of the order of 0.1 Torr.

5. A method according to claim 4 wherein said chopping frequency is of the order of 100 kHz.

6. A method according to claim 1 wherein said chopping frequency is greater than 50 kHz.

7. A method according to claim 1 wherein said chopping frequency is of the order of 100 kHz.

8. A method according to claim 2 wherein said open cathode comprises a planar cathode.

9. A method of determining isotopic abundances for a sample comprising generating a sputtered vapour of the sample in an evacuated sputtering cell and obtaining a saturated absorption spectrum for the vapour, wherein said vapour is sputtered from a cathode including the sample, and the pressure in said sputtering cell and the chopping frequency of an incident laser beam employed to obtain said spectrum are selected to reduce the number of detected velocity-changing collisions in said cell to substantially eliminate any background Doppler-broadened component from said saturated absorption spectrum, which is thereby a substantially Doppler-free spectrum for the sample, having discrete lines identifiable with respective isotopes of the sample, said method further comprising calculating the isotopic abundances from the intensities of said lines, with corrections as necessary for effects dependent on density of absorbing atoms in the cell, laser intensity, differences in isotopic mass, and, with isotopes having nuclear spin, hyperfine structure.

10. A method according to claim 9 wherein said vapour is sputtered from an open cathode including the sample.

11. A method according to claim 9 wherein said pressure in said sputtering cell is less than 10 Torr.

12. A method according to claim 9 wherein said pressure in said sputtering cell is of the order of 0.1 Torr.

13. A method according to claim 12 wherein said chopping frequency is of the order of 100 kHz.

14. A method according to claim 9 wherein said chopping frequency is greater than 50 kHz.

15. A method according to claim 9 wherein said chopping frequency is of the order of 100 kHz.

16. A method according to claim 10 wherein said open cathode comprises a planar cathode.

17. Apparatus for obtaining a substantially Doppler-free spectrum of a sample, comprising:
   a sputtering cell having a sputtering cathode of the sample for generating in a vacuum in the cell a sputtered vapour of the sample;
   a spectroscopic arrangement to obtain a saturated absorption spectrum of the vapour in the cell, said arrangement including means to chop an incident light beam for said cell, and means for controlling, in use, the pressure in said sputtering cell and the chopping frequency of an incident beam employed to obtain said spectrum to reduce the number of detected velocity-changing collisions in said cell to substantially eliminate any background Doppler-broadened component from said saturated absorption spectrum, which is thereby a substantially Doppler-free spectrum.

18. Apparatus according to claim 17 wherein said sputtering cathode comprises a planar cathode.

* * * * *